(12) United States Patent
Forlin et al.

(10) Patent No.: US 7,138,534 B2
(45) Date of Patent: Nov. 21, 2006

(54) PROCESS FOR THE CONTINUOUS PRODUCTION OF AN OLEFINIC OXIDE

(75) Inventors: Anna Forlin, Vigonza (IT); Paolo Tegon, Oriago (IT); Giuseppe Paparatto, Cinisello (IT)

(73) Assignee: Dow Global Technologies Inc., Midland, MI (US)

( * ) Notice: Subject to any disclaimer, the term of this patent is extended or adjusted under 35 U.S.C. 154(b) by 359 days.

(21) Appl. No.: 10/344,441

(22) PCT Filed: Aug. 13, 2001

(86) PCT No.: PCT/EP01/09334

§ 371 (c)(1),
(2), (4) Date: Oct. 27, 2003

(87) PCT Pub. No.: WO02/14298

PCT Pub. Date: Feb. 21, 2002

(65) Prior Publication Data

US 2004/0181081 A1    Sep. 16, 2004

(30) Foreign Application Priority Data

Aug. 11, 2000  (IT) .......................... MI2000A1882

(51) Int. Cl.
*C07D 301/12*    (2006.01)
(52) U.S. Cl. ................................... 549/531
(58) Field of Classification Search ................. 549/531
See application file for complete search history.

(56) References Cited

U.S. PATENT DOCUMENTS

| | | | |
|---|---|---|---|
| 4,410,501 A | 10/1983 | Taramasso et al. ......... | 423/326 |
| 4,656,019 A | 4/1987 | Hensler et al. ............. | 423/315 |
| 4,666,692 A | 5/1987 | Taramasso et al. ......... | 423/326 |
| 4,824,976 A | 4/1989 | Clerici et al. ............... | 549/531 |
| 4,859,785 A | 8/1989 | Bellussi et al. ............. | 549/531 |
| 4,937,216 A | 6/1990 | Clerici et al. ................. | 502/62 |
| 5,695,736 A * | 12/1997 | Saxton et al. ............... | 423/700 |
| 6,300,506 B1 | 10/2001 | Paparatto et al. ........... | 549/531 |

FOREIGN PATENT DOCUMENTS

| | | |
|---|---|---|
| BE | 1001038 | 6/1989 |
| EP | 100119 | 8/1984 |
| EP | 226257 | 6/1987 |
| EP | 226258 | 6/1987 |
| EP | 230949 | 8/1987 |
| EP | 266825 | 5/1988 |
| EP | 315247 | 5/1989 |
| EP | 568336 | 11/1993 |
| EP | 568337 | 11/1993 |
| EP | 712852 | 5/1996 |
| EP | 940393 | 9/1999 |
| EP | 1074548 | 2/2001 |
| ES | 2037596 | 6/1993 |
| WO | WO 9901445 | 1/1999 |
| WO | WO 0017178 | 3/2000 |

OTHER PUBLICATIONS

Serrano, et al.; "Synthesis of Titanium—Containing ZSM-48;" Journal of Chemical Communications; 1992; p. 745-747.

* cited by examiner

*Primary Examiner*—Golamm M. Shameem
*Assistant Examiner*—Ebenezer Sackey (57) ABSTRACT

A process for the continuous production of an olefinic oxide such as propylene oxide by direct catalytic oxidation of an olefin with hydrogen peroxide. The process involves successive reaction, distillation, decomposition, phase, separation, condensation and distillation with recycle of various streams to provide improved catalyst life and reaction selectivity.

49 Claims, 1 Drawing Sheet

Fig. 1

US 7,138,534 B2

PROCESS FOR THE CONTINUOUS PRODUCTION OF AN OLEFINIC OXIDE

The present invention relates to a process for the continuous production of an olefinic oxide, for example propylene oxide, ethylene oxide and butylene oxide. More particularly, the present invention relates to a process for the continuous production of propylene oxide by direct oxidation of propylene with hydrogen peroxide.

Olefin oxides, hereafter referred to as epoxides, are intermediates that are useful for preparing a wide variety of compounds. Thus, for example, epoxides may be used to produce glycols, condensation polymers such as polyesters, or for the preparation of intermediates that are useful in the synthesis of polyurethane foams, elastomers, sealants and the like.

It is known to prepare epoxides by direct oxidation of olefinic compounds with hydrogen peroxide in the presence of suitable catalysts.

The catalysts generally used are zeolite compounds in a modified form (EP 100 119) or suitably treated with a neutralizing agent whose function is to neutralize the acidic groups present on the surface of the catalyst, which may promote side reactions of degradation of the epoxide.

Thus, for example, EP-A-230 949 describes an epoxidation process which uses as catalyst a titanium silicalite treated, before or during the reaction, with a neutralizing agent chosen from organosilicon derivatives of the type $X-SiR_3$ or water-soluble substances derived from cations of groups I and II of difference basic strength.

EP-A-712 852 describes a process for epoxidizing olefins in the presence of titanium silicalite which uses as neutralizing agent a non-basic salt chosen from lithium chloride, sodium nitrate, potassium sulphate and ammonium phosphate.

EP-A-940 393 describes a process for synthesizing epoxides in which the titanium silicalite used as catalyst is treated, before it is used, with organic molecules containing a substituted amide group. Working according to the said process gives an $H_2O_2$ conversion of 90% and a selectivity towards epoxide of 91%.

WO 00/17178 describes a process in which titanium silicalite is used in the presence of low concentrations of a tertiary amine and/or a tertiary amine oxide.

Although these catalysts show good activity and selectivity when freshly prepared, they however show a gradual deactivation in the course of the epoxidation reaction, with a reduction in the yields of epoxide over time, due substantially to the decrease in the conversion of the hydrogen peroxide.

The need for frequent removal and/or recovery and regeneration of the catalyst makes these processes difficult to use industrially. In addition, the relatively mediocre selectivity makes it necessary to recover and dispose of substantial amounts of by-products.

In addition, a zeolite-based catalyst subjected to frequent thermal regeneration cycles generally tends to become degraded, in particular when alkali metals such as sodium or potassium that are still present, even in small amounts, remain absorbed on the structure, in the reaction reagents.

To overcome these problems, a number of processes make use of particular reactor-based solutions or of particular operating conditions.

For example, WO 99/01445 describes a process for epoxidizing propylene in the presence of titanium silicalite, in which the temperature and pressure are increased in the course of the epoxidation reaction, so as to maintain a high efficiency of the catalytic system.

By working according to this process, after 85 hours, the catalyst begins to decay and needs to be separated out and regenerated.

The Applicant has now found that, by using suitable operating conditions in the reaction between an olefin and hydrogen peroxide, it is possible to keep the catalytic activity stable over time, thus reducing and desirably minimizing the frequency of the regeneration cycles, and to obtain high yields of epoxides, maintaining over time a high conversion and selectivity with respect to the hydrogen peroxide and producing the epoxide with a high production efficiency and a high degree of purity.

Thus, one object of the present invention is a process for the continuous preparation of an olefinic oxide by direct oxidation of an olefin with hydrogen peroxide, which comprises:

(a) feeding into a reaction zone, preferably comprising a reaction unit comprising one or more reactors placed in series, containing an epoxidation catalyst, preferably suspended in a reaction solvent, the olefin, the hydrogen peroxide, and a buffer and a reaction solvent;

(b) feeding the product of the reaction zone which suitably is filtered and in the liquid phase into a distillation zone, preferably comprising a distillation unit comprising one or more stripping (flash) columns and more especially one stripping column for each reactor of the reaction unit, to obtain a head product comprising olefinic oxide and unreacted olefin, and a tail product comprising unreacted hydrogen peroxide, reaction by-products and water and reaction solvent;

(c) feeding the tail product of the distillation zone and an aqueous basic solution into a decomposition zone, preferably comprising a decomposition unit R-4A/B comprising one or more reactors placed in series, containing a decomposition catalyst which preferably is supported and decomposes hydrogen peroxide in the tail product suitably to oxygen and water;

(d) feeding the mixture leaving the decomposition zone, preferably units R-4A/B, comprising oxygen water and solvent, optionally together with an inert gas, into a phase separation zone, preferably a phase separator V-4, to obtain at the top a gaseous phase containing oxygen, traces of solvent and optionally an inert gas, and at the bottom a liquid phase comprising water and reaction by-products and solvent,;

(e) feeding the gaseous phase leaving the phase separation zone into a condensation zone, preferably comprising a condensation system comprising one or more condensers in series, to recover the residual solvent, and discharging the uncondensable compounds (oxygen with traces of solvent and optionally inert gas);

(f) feeding the liquid phase leaving the phase separation zone and the solvent leaving the condensation zone into a further distillation zone, preferably a column C6, to obtain at the top a solvent which is recycled into the reaction zone in step (a), and a tail product comprising water, suitably the reaction water and of the water introduced with the hydrogen peroxide, the reaction by-products and the traces of solvent, which tail product is discarded;

(g) feeding the head product from the distillation zone in step b), together with the vent products from the reactor zone in step a), into a further distillation zone, preferably a column C4, to obtain a head product comprising unreacted olefin, which is recycled into the reaction zone in step a), and a tail product comprising the olefinic oxide;

(h) feeding the tail product from the distillation zone in step g) into a purification zone, for example purification section C5, to recover the residual olefin, which is recycled into the reaction zone in step a), a liquid phase comprising solvent, which is recycled into the distillation zone in step b) and the olefinic oxide, desirably of commercial purity.

According a further aspect, the invention provides a process comprising:

(a) feeding into a first reactor R1, in which is contained a catalyst comprising a titanium-containing zeolite held in suspension in liquid reaction medium, a first portion of an olefin charge, hydrogen peroxide, a solvent and a buffer;

(b) filtering the liquid product from the first reactor R1 and feeding the filtered product into a first column C1 to obtain a head product comprising olefinic oxide and unreacted olefin, and a tail product comprising solvent, water and unreacted hydrogen peroxide;

(c) feeding the tail product from the first column C1, together with a second portion of the olefin charge, hydrogen peroxide and buffer, into a second reactor R2;

(d) filtering the liquid product from the second reactor R2 and feeding the filtered product into a second stripping column C2 to obtain a head product comprising olefinic oxide and unreacted olefin and a tail product comprising solvent and residual hydrogen peroxide;

(e) feeding the tail product from the second column C2, a third portion of the olefin charge and buffer into a third reaction unit R3;

(f) filtering the liquid product from the third reactor R3 and feeding the filtered product into a third stripping column C3 to obtain a head product comprising olefinic oxide and unreacted olefin, and a tail product comprising solvent, water and traces of hydrogen peroxide;

(g) feeding into a decomposition unit R-4A/B preferably comprising two reactors placed in series, containing a supported catalyst for decomposing the residual hydrogen peroxide to $O_2$ and $H_2O$, the tail product from the third column C3 and an aqueous basic solution;

(h) feeding into a phase separator (flash) V-4, the mixture leaving the decomposition unit R-4A/B, comprising solvent, oxygen, and water, together with an inert gas, preferably nitrogen, to obtain a liquid phase comprising solvent, water and reaction by-products and a gaseous phase comprising solvent, oxygen and inert gas; the amount of inert gas fed in is such as to keep the aqueous phase below the lower flammability limit;

(i) feeding the gaseous phase leaving V4 into a condensation system, preferably comprising two condensers in series E-421 and E-422 to recover the entrained solvent, while the uncondensable compounds (oxygen and inert gas) are discharged;

(j) feeding the solvent leaving the condensation system, together with the liquid phase leaving V4, into a distillation column C6 to obtain at the top the solvent, which is recycled into the reaction unit (R1), and a tail product comprising the reaction water and water introduced with the hydrogen peroxide, the reaction by-products and the traces of solvent, which is discarded;

(m) feeding the head product from the stripping column C1–C3, together with the reactor vent products, into a distillation column C4 to obtain a head product comprising the unreacted olefin, which, suitably except for a small bleed to keep constant the titre of the hydrogenated olefin, for example propane, is recycled into one or more of the reaction units R1 to R3, and a tail product comprising the olefinic oxide and traces of solvent and of unreacted olefin;

(n) feeding the tail product from the distillation column into a purification section, preferably comprising two columns in series (C-5A and C-5B), to recover, preferably from the column head, unreacted residual olefin, which is recycled into one or more of the reaction units R1 to R3 suitably from a withdrawal line close to the column head, olefinic oxide of commercial purity, and from the column tail, a liquid phase comprising solvent and olefinic oxide, which is recycled into the distillation column C3.

Olefins which may be used in the process of the present invention are those of general formula (I)

in which: $R_1$, $R_2$, $R_3$ and $R_4$, which may be identical or different, may be hydrogen, an alkyl radical containing from 1 to 20 carbon atoms, an aryl radical, an alkylaryl radical containing from 7 to 20 carbon atoms, a cycloalkyl radical containing from 6 to 10 carbon atoms or an alkylcycloalkyl radical containing from 7 to 20 carbon atoms.

The radicals $R_1$, $R_2$, $R_3$ and $R_4$ may constitute pairs of saturated or unsaturated rings. In addition, the said radicals may contain halogen atoms, nitro or nitrile groups, sulphonic groups and esters thereof, carbonyl, hydroxyl, carboxylic, thiol, amine and ether groups.

The olefins may bear the substituents mentioned above either on the unsaturated carbon atoms or on other positions.

Non-limiting examples of olefins of formula (I) are: ethylene, propylene, allyl chloride, allyl alcohol, butenes, pentenes, hexenes, 1-hepteneoctene, 1-tridecene, mesityl oxide, isoprene, cyclooctene, cyclohexene or bicyclic compounds such as norbornenes, pinenes, etc.

The preferred olefin is propylene. Generally, propylene is used in a purity of greater than 70%. Preferably, propylene is available as a steam-cracking stream in a minimum purity of 96%, the remainder comprising propane and typical $C_3$ impurities.

The oxidizing agent used in the process of the present invention suitably is hydrogen peroxide ($H_2O_2$) or a compound which is capable of generating $H_2O_2$ under the epoxidation conditions.

Preferably, an aqueous hydrogen peroxide solution at a minimum concentration of 1% by weight is used, preferably with titre of greater than or equal to 35% by weight The amount of hydrogen peroxide relative to the olefin is not critical, but it is preferable to use an olefin/$H_2O_2$ molar ratio of between 10:1 and 1:10 and preferably between 6:1 and 1:1.

The epoxidation reaction may be carried out in one or more solvents that are liquid at the epoxidation temperatures, that are compatible with hydrogen peroxide and that are capable of dissolving the olefin and the olefinic oxide produced.

Typically, solvents of polar nature are used, such as: alcohols, aqueous-alcoholic mixtures, ketones, ethers, esters, aliphatic, cycloaliphatic or aromatic hydrocarbons, halogenated hydrocarbons, or mixtures thereof.

Examples of alcohols that are suitable for the process of the present invention are methanol, ethanol, isopropyl alcohol, t-butyl alcohol and cyclohexanol. Examples of ketones are acetone, methyl ethyl ketone and acetophenone. Examples of ethers are tetrahydrofuran and butyl ether.

Preferably, methanol and, among the ketones, acetone are used. The methanol/water mixture with a weight ratio between the two compounds of between 10/90 and 99/1 is particularly preferred.

The buffer suitably is chosen from aqueous ammonia, ammonium acetate, ammonium formate or a system comprising a nitrogenous base and a salt thereof with an organic or mineral acid, as described in Italian patent application No. MI 99A/001658.

Suitably, the buffer is fed continuously with one of the reagent flows fed into the epoxidation reactor, in an amount such as to maintain the pH of the reaction mixture, measured under the working conditions, at a value above 5 and preferably between 5.5 and 8.

The epoxidation catalyst which may be used in the process of the present invention suitably is chosen from those generally known as titanium silicalites although other known epoxidation catalysts may be employed as desired.

For example, the titanium silicalites MFI structure may be used, which are described in U.S. Pat. No. 4,410,501, in which their structural properties are also reported.

Titanium silicalites in which some of the titanium is replaced with other metals such as boron, aluminium, iron or gallium may also be used. These substituted titanium silicalites and the methods for preparing them are described in EP-A-226 257, EP-A-226 258 and EP-A-266 825.

Titanium silicalites of MEL or intermediate MFI/MEL structure, described in Belgian patent 1 001 038, may also be used. Other titanium silicalites may be chosen from titanium-containing β-zeolites of BEA structure, described in Spanish patent 2 037 596, and zeolites ZSM-12 containing titanium and optionally aluminium, described in "Journal of Chemical Communications, 1992, page 745".

A catalyst which is preferred according to the present invention is the titanium silicalite of general formula (II):

$$xTiO_2 \cdot (1-x)SiO_2$$

in which x represents a number between 0.0001 and 0.04, preferably the value of x is between 0.01 and 0.025, which are described, for example, in U.S. Pat. No. 4,410,501, U.S. Pat. No. 4,824,976, U.S. Pat. No. 4,666,692, U.S. Pat. No. 4,656,016, U.S. Pat. No. 4,859,785 and U.S. Pat. No. 4,937,216.

The catalyst may be used in the form of powder, pallets, microspheres, an extrudate or other suitable physical forms.

The use of a binder (co-gel) or of an inert support in combination with the catalyst may be advantageous. Supported catalysts may be prepared using known methods.

The inert support may typically consist of silica, alumina, silica-alumina, zeolites, active charcoal and other materials that are well known in a state of the art.

The amount of catalyst used in the process of the invention is not critical; however, it is chosen so as to allow the epoxidation reaction to proceed to completion in the shortest possible time.

Generally, the amount of catalyst will be chosen as a function of various parameters, such as the reaction temperature, the reactivity and concentration of the olefin, the concentration of hydrogen peroxide, the type and composition of the solvents, the catalytic activity and the type of reactor or of reaction system used.

Typically, the amount of catalyst will be between 1% and 15% by weight relative to the reaction mixture and preferably between 4% and 10% by weight.

The temperature used in the process of the present invention is generally between 20° C. and 150° C., preferably between 40° C. and 100° C. and particularly preferably between 55° C. and 90° C.

The pressure at which the process is performed is that which allows the olefin to be maintained in the liquid phase at the chosen reaction temperature. In general, the process is performed at a pressure greater than atmospheric pressure when gaseous olefins are used.

The reactor used in the epoxidation reaction may be any reactor capable of operating continuously and of carrying out the reaction in a system such as the one described, achieving an efficient contact between the olefin, the liquid phase and the catalyst held in suspension.

Examples of reactors that are suitable for this purpose are stirred reactors, bubble reactors, gas-lift reactors with internal or external circulation or CSTRs (Continuous Stirred Tank Reactors) or PFRs (Plug Flow Reactors), as described in the prior art.

Preferably, the reactors R1–R3 are of the CSTR type and are isothermic.

The olefin charge, by which is meant the fresh olefin, the recycled olefin or mixtures thereof, is fed into the reaction stage (R1–R3) at a controlled throughput and in excess to maximize the conversion end selectivity towards olefinic oxide and to maintain the reaction pressure. Preferably, the three reactors R1–R3 are fed with a mixture consisting of fresh olefin originating from the amount in storage and from a recycled olefin.

According to one embodiment of the process of the present invention, before introducing the fresh olefin into the reactors R1–R3, it is purified in the distillation column C4.

The feed of hydrogen peroxide may be divided into two portions such that the ratio of the feeds to the reactors R1 and R2 is between 90:10 and 10:90 and preferably between 60:40 and 40:60. A 50:50 ratio is particularly preferred.

The reactors R1 and R2 operate under substantially identical conditions, that is to say at a temperature of about 55–750° C. and at a pressure of 13 bar, while the reactor R3, which works as the finishing reactor, that is to say the reactor which depletes the hydrogen peroxide fed to the reactors R1 and R2, operates at a temperature of 70–90° C. and at a pressure of 8 bar.

The overall oxidation reaction of the olefin is carried out so as to have in the stream leaving the unit R3 an $H_2O_2$ concentration of less than 100 ppm.

In the first reactor, the reaction selectivity towards the hydrogen peroxide is preferably 98 mol % with a 96% conversion, in the second reactor the reaction selectivity towards the hydrogen peroxide is preferably 97.8 mol % with a 95% conversion, and in the third reactor the selectivity is preferably 80 mol % with a 95% conversion.

Suitably the distillation (flash) columns operate substantially under the same operating conditions and discharge at the top streams in vapour phase comprising unreacted olefin, olefinic oxide, inert gases, for example aliphatic hydrocarbons, for instance propane, and solvent vapours. At the bottom, the columns discharge streams in liquid phase of differentiated composition.

Suitably the head vapours from columns C1–C3 are fed into a distillation column C4 to recover, at the top, the unreacted olefin. This olefin is preferably recycled into the synthesis of the olefinic oxide after partial removal of the inert gases. Column C4 is suitably also fed with vapours of the vent gases from the reactors R1–R3.

The temperature at the bottom of column C4 should not exceed 80° C. with residence times in the region of one minute, so as to avoid degradation of the olefinic oxide.

Whereas the tailstreams from the distillation columns C1 and C2 still may contain substantial amounts of hydrogen peroxide and are therefore recycled into the synthesis of the olefinic oxide, the tailstream from column C3 is suitably substantially free of $H_2O_2$ and comprises solvent, water and reaction by-products.

Suitably this stream is fed into a section for decomposition of the residual hydrogen peroxide, together with an aqueous solution of alkali metal or alkaline-earth metals hydroxides or carbonates to control the pH of the $H_2O_2$ decomposition reaction to values>10 and to avoid the formation of light by-products derived from the oxidation of the solvent and from the degradation of the epoxide. For example, when the solvent used in the epoxidation reaction is methanol, these by-products are methyl formate and dimethoxymethane.

Preferably, the decomposition reactors R-4A/B are fixed-bed tubular reactors arranged in series.

The decomposition reaction of the hydrogen peroxide is exothermic and suitably takes place in the liquid phase at about 80° C.–90° C., with a residence time of between 1 and 10 minutes and preferably between 2 and 5 minutes.

Examples of catalysts used in the decomposition reaction consist of group VIII metals or oxides thereof. The supports are desirably selected from those of the prior art which are mentioned above.

The mixture leaving R-4A/B is preferably fed into a phase separator V-4 in which the oxygen generated by the decomposition of the hydrogen peroxide is separated from the inert diluent gas, preferably nitrogen, introduced downstream of the reactor R-4B to keep the solvent/oxygen mixture released in the flash column below the lower flammability limit.

Suitably, the solvent-oxygen-inert gas mixture leaving V-4 is then condensed in the two condensers in series E-421 and E-422 to recover the solvent, while the uncondensable materials (oxygen and inert gas with traces of solvent) are discharged.

The liquid mixture leaving V-4 is preferably fed into the distillation column C6, at the top of which is recovered the solvent, which is then recycled, while from the bottom the water (reaction water and the water from the $H_2O_2$ solution) and the by-products are discarded.

The heat of condensation recovered at the top of column C6 may be used to serve some or all the boiling needs present in the process. In this case, the column pressure is maintained at a value which is suitable for this purpose.

Suitably a liquid stream rich in olefinic oxide is extracted from the bottom of the distillation column C4 and is conveyed to a purification section C5. Preferably, this section consists of two columns that are in series on account of the large number of plates (99) and separates out at the top residual vapours that are still present (unreacted olefin and inert gases), at the bottom a liquid stream containing solvent and olefinic oxide (recycled into the distillation column C3) and, laterally, liquid stream consisting of olefinic oxide of commercial purity. By commercial purity is meant a purity level of at least 99.8%.

The vapours extracted from the top of the purification column C5 may still contain significant amounts of olefinic oxide and suitably are recycled upstream of the distillation column C4.

By working according to the process of the present invention, the catalyst suitably shows fewer signs of decay after 1000 hours than when employed in a convention process for the production of an olefin oxide and desirably shows insignificant or no signs of decay after 1000 hours and the production efficiency and reaction selectivity are high.

Figure 1:
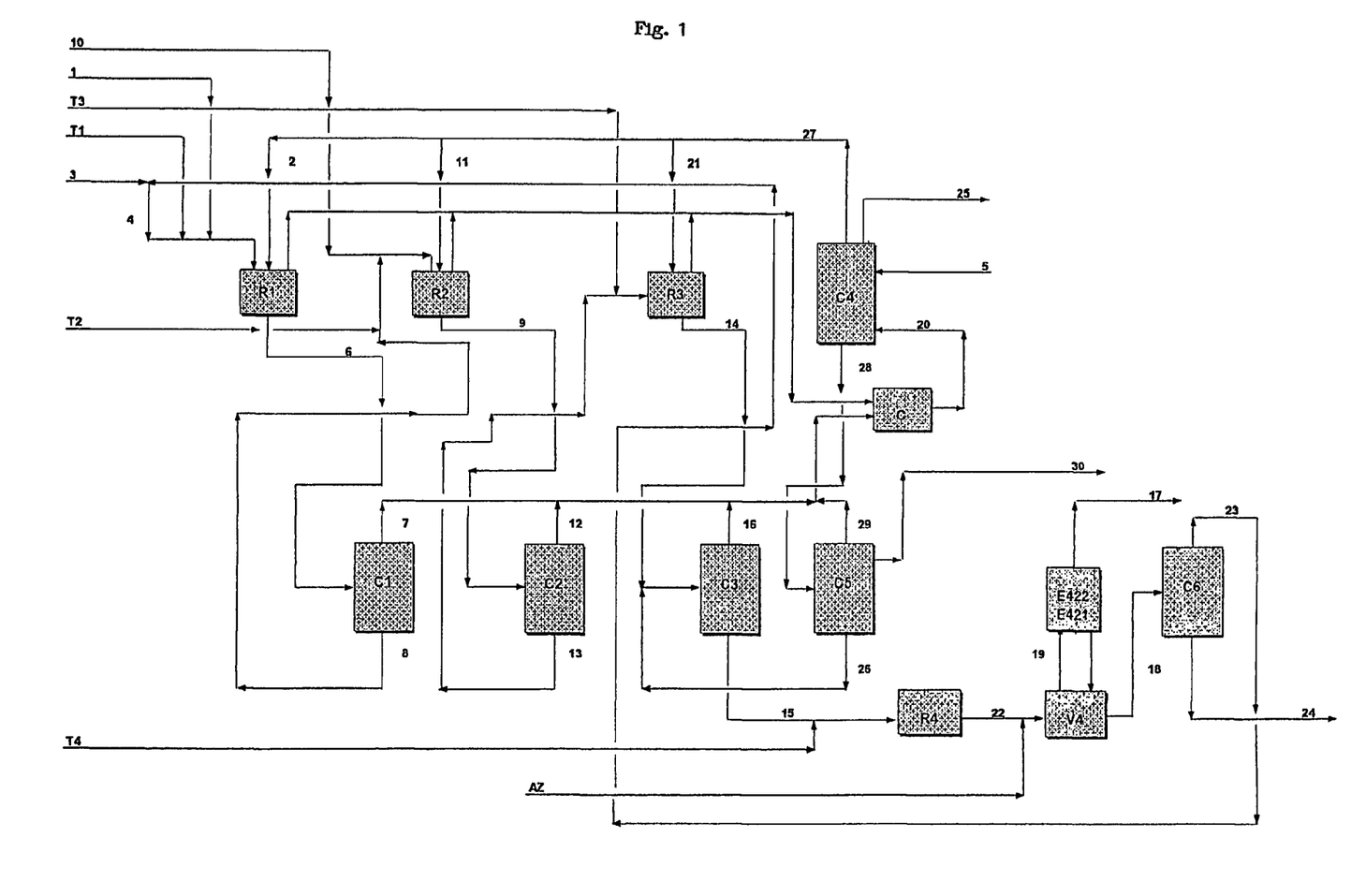

The process for preparing olefinic oxides may be understood more clearly with reference to the block diagrams in FIG. 1, which represent an illustrative and non-limiting embodiment.

With reference to FIG. 1, R1, R2 and R3 represent reactors of CSTR type arranged in series, C1, C2 and C3 represent three stripping columns associated with the reactors R1–R3 for recovery of the olefinic oxide produced, C4 represents a distillation column for recovery and recycling of the unreacted olefin; C5 represents a distillation column for purifying the olefinic oxide; C6 represents a distillation column for recovering/recycling the reaction solvent and for discharging the water and the reaction by-products, E represents a condenser for condensing the olefinic oxide entrained by the recycled olefin, and C represents a compressor for bringing the recycled olefin to the working pressure of the synthesis reactors.

With reference to FIG. 1, the olefin, for example propylene, is fed in parallel into reactors R1–R2–R3 via the lines (2)–(11)–(21). The hydrogen peroxide is fed in parallel into R1–R2 via the lines (1) and (11); the buffer is fed into the reactors R1–R2–R3 in parallel via the lines (T1)–(T2)–(T3), while the recycled solvent (4) is fed entirely into the reactor R1. Any losses of solvent in the production cycle are replaced by means of the "make-up" line (3).

The filtered liquid reaction product leaving the first reactor R1 is fed via the line (6) into the first distillation column C1, from the top of which is recovered the propylene oxide produced (7), in the vapour phase, and from the bottom of which is recovered a liquid stream (8) still containing hydrogen peroxide, fed into the reactor R2.

The filtered liquid reaction product leaving the second reactor R2 is fed via the line (9) into the second distillation column C2, from the top of which is recovered the propylene oxide produced (12), in the vapour phase, and from the bottom of which is recovered a liquid stream (13) still containing hydrogen peroxide, which is fed into the reactor R3.

The filtered liquid reaction product leaving the third reactor R3 is fed via the line (14) into the third distillation column C3, from the top of which is recovered the propylene oxide produced (16), in the vapour phase, and from the bottom of which is fed a liquid stream (15) still containing hydrogen peroxide, which is fed into the reactor R4.

The basic solution (T4) is also fed into R4. The liquid reaction product leaving the reactor R4 is fed via the line (22) into the flash tank V4, the vapour phase of which is sent to two condensers in series E421–E422 via the line (19); the gaseous discharge from E422 into the atmosphere, containing oxygen, nitrogen and traces of methanol, is represented the line (17). The diluent nitrogen is fed into V4 via the line (AZ).

The operating example given below is for purely illustrative purposes and is non-limiting.

EXAMPLE 1

The process is performed according to the scheme in FIG. 1 to produce propylene oxide from:
- a stream originating from a steam-cracking plant, consisting of 99.5% by weight of propylene and 0.05% by weight of propane;
- an aqueous solution of hydrogen peroxide at 35% by weight;
- methanol.

The catalyst is titanium silicalite, of the type described in patent U.S. Pat. No. 4,937,216, and is present in reactors R1, R2 and R3 in a respective concentration of 6% by weight relative to the slurry.

The buffer consists of an aqueous $NH_4OH$ solution and is fed into the stream of methanol entering the reactor in an amount such as to buffer the pH of the reaction mixture to a value of 6.5 (present in the total liquid flow in a concentration of 60 ppm). A toughened-glass pH-meter is used, which is inserted into the reaction flow.

The bed of catalyst in the decomposition column R4, in the form of pallets with an active phase of 15%, is loaded in excess volume to ensure the depletion of the hydrogen peroxide.

The attached Tables 1-A and 1-B give the balances and the composition of the individual streams.

TABLE 1-A

| COMPONENTS | 1 (kg/h) | 1 (%) | 2 (kg/h) | 2 (%) | 3 (kg/h) | 3 (%) | 4 (kg/h) | 4 (%) |
|---|---|---|---|---|---|---|---|---|
| Propylene | | | 411.63 | 83.94 | | | | |
| Propane | | | 26.54 | 6.06 | | | | |
| Propylene Oxide (PO) | | | | | | | 0.00 | 0.00 |
| Methanol (MeOH) | | | 0.00 | 0.00 | 3.70 | 100.00 | 2069.16 | 97.00 |
| Water ($H_2O$) | 146.2500 | 65.00 | 0.00 | 0.00 | | | 64.00 | 3.00 |
| Hydrogen Peroxide ($H_2O_2$) | 78.7500 | 35.00 | 0.00 | 0.00 | 0.00 | 0.00 | 0.00 | 0.00 |
| Methoxypropanol | | | 0.00 | 0.00 | 0.00 | 0.00 | 0.00 | 0.00 |
| 1,2-prapanediol | | | 0.00 | 0.00 | 0.00 | 0.00 | 0.00 | 0.00 |
| THROUGHPUT | 225.0 | 100 | 438.2 | 100 | 3.7 | 100 | 2133.2 | 100 |
| Temperature | 30.00 | | −14.60 | | 35.00 | | 35.00 | |
| Pressure | 16.00 | | 16.00 | | 16.00 | | 16.00 | |

| COMPONENTS | 5 (kg/h) | 5 (%) | 6 (kg/h) | 6 (%) | 7 (kg/h) | 7 (%) | 8 (kg/h) | 8 (%) |
|---|---|---|---|---|---|---|---|---|
| Propylene | 207.3 | 99.50 | 318.2 | 11.38 | 318.2 | 60.48 | 0.0 | 0.00 |
| Propane | 1.035 | 0.60 | 26.5 | 0.95 | 26.5 | 5.04 | 0.0 | 0.00 |
| Propylene Oxide (PO) | | | 128.4 | 4.62 | 126.4 | 24.02 | 0.000 | 0.00 |
| Methanol (MeOH) | | | 2068.0 | 73.95 | 55.0 | 10.45 | 2013.0 | 88.67 |
| Water ($H_2O$) | | | 250.1 | 8.94 | 0.0 | 0.00 | 250.1 | 11.02 |
| Hydrogen Peroxide ($H_2O_2$) | | | 3.2 | 0.11 | 0.0 | 0.00 | 3.2 | 0.14 |
| Methoxypropanol | | | 3.2 | 0.11 | 0.0 | 0.00 | 3.2 | 0.14 |
| 1,2-prapanediol | | | 0.7 | 0.02 | 0.0 | 0.00 | 0.7 | 0.03 |
| THROUGHPUT | 208.3 | 100 | 2796.3 | 100 | 526.2 | 100 | 2270.2 | 100 |
| Temperature | 37.60 | | 60.00 | | 36.60 | | 84.30 | |
| Pressure | 16.00 | | 13.00 | | 1.80 | | 1.94 | |

| COMPONENTS | 17 (kg/h) | 17 (%) | 18 (kg/h) | 18 (%) | 19 (kg/h) | 19 (%) | 20 (kg/h) | 20 (%) |
|---|---|---|---|---|---|---|---|---|
| Propylene | | | | | | | 754.08 | 54.77 |
| Propane | 0.0 | 0.00 | | | | | 61.44 | 4.46 |
| Propylene Oxide (PO) | 0.0 | 0.00 | 0.0 | 0.00 | | | 415.52 | 30.18 |
| Methanol (MeOH) | 0.6 | 36.22 | 2065.5 | 81.92 | 146.8 | 91.24 | 145.00 | 10.53 |
| Water ($H_2O$) | 0.003 | 0.17 | 445.3 | 17.66 | 12.9 | 8.04 | 0.77 | 0.06 |
| Hydrogen Peroxide ($H_2O_2$) | | | 0.0 | 0.00 | | | 0.00 | 0.00 |
| Methoxypropanol | | | 8.63 | 0.34 | 0.1 | 0.04 | 0.00 | 0.00 |
| 1,2-prapanediol | | | 1.82 | 0.07 | 0.001 | 0.00 | 0.00 | 0.00 |
| Oxygen | 0.1 | 6.74 | | | 0.10 | 0.06 | | |
| NH4OH | | | | | | | | |
| NaOH | | | | | | | | |
| Nitrogen | 1.0 | 57.86 | 0.000 | 0.00 | 1.000 | 0.62 | 0.103 | 0.01 |
| THROUGHPUT | 1.7 | 100 | 2521.2 | 100 | 160.9 | 100 | 1376.9 | 100 |
| Temperature | −15.00 | | 67.30 | | 67.30 | | 40.00 | |
| Pressure | 1.10 | | 1.20 | | 1.20 | | 4.00 | |

| COMPONENTS | 21 (kg/h) | 21 (%) | 22 (kg/h) | 22 (%) | 23 (kg/h) | 23 (%) | 24 (kg/h) | 24 (%) |
|---|---|---|---|---|---|---|---|---|
| Propylene | 200.0 | 93.94 | 0.00 | 0.00 | | | | |
| Propane | 12.9 | 6.06 | 0.00 | 0.00 | | | | |
| Propylene Oxide (PO) | | | 0.001 | 0.00 | 0.00 | 0.00 | | |
| Methanol (MeOH) | | | 2068.09 | 81.92 | 2065.5 | 96.99 | 0.0 | 0.00 |
| Water ($H_2O$) | | | 445.31 | 17.66 | 64.00 | 3.01 | 381.3 | 97.33 |
| Hydrogen Peroxide ($H_2O_2$) | | | 0.00 | 0.00 | | | | |
| Methoxypropanol | | | 8.63 | 0.34 | 0.00 | 0.00 | 8.63 | 2.20 |
| 1,2-prapanediol | | | 1.82 | 0.07 | | | 1.82 | 0.47 |
| Oxygen | | | 0.10 | 0.004 | | | | |
| NH4OH | | | | | | | | |
| NaOH | | | | | | | | |
| Nitrogen | | | | | 0.02 | 0.00 | | |

TABLE 1-A-continued

| | | | | | | | | |
|---|---|---|---|---|---|---|---|---|
| THROUGHPUT | 212.9 | 100 | 2522.0 | 100 | 2129.5 | 100 | 391.8 | 100 |
| Temperature | −14.50 | | 89.8 | | 87.00 | | 128.60 | |
| Pressure | 16.00 | | 10 | | 2.50 | | 2.66 | |

TABLE 1-B

| | 9 | | 10 | | 11 | | 12 | |
|---|---|---|---|---|---|---|---|---|
| COMPONENTS | (kg/h) | (%) | (kg/h) | (%) | (kg/h) | (%) | (kg/h) | (%) |
| Propylene | 237.8 | 8.31 | | | 336.79 | 93.94 | 237.8 | 54.22 |
| Propane | 21.7 | 0.76 | | | 21.7 | 6.06 | 21.7 | 4.95 |
| Propylene Oxide (PO) | 133.69 | 4.67 | | | | | 133.69 | 30.48 |
| Methanol (MeOH) | 2011.7 | 70.32 | | | | | 46.0 | 10.26 |
| Water (H$_2$O) | 443.15 | 15.49 | 150.8000 | 65.00 | | | 0.38 | 0.09 |
| Hydrogen Peroxide (H$_2$O$_2$) | 4.2 | 0.15 | 81.2000 | 35.00 | | | 0.0 | 0.00 |
| Methoxypropanol | 6.9 | 0.24 | | | | | 0.0 | 0.00 |
| 1,2-propanediol | 1.5 | 0.05 | | | | | 0.0 | 0.00 |
| THROUGHPUT | 2860.7 | 100 | 232.0 | 100 | 358.5 | 100 | 438.6 | 100 |
| Temperature | 50.00 | | 30.00 | | −14.50 | | 50.00 | |
| Pressure | 13.00 | | 16.00 | | 16.00 | | 16.00 | |

| | 13 | | 14 | | 15 | | | |
|---|---|---|---|---|---|---|---|---|
| COMPONENTS | (kg/h) | (%) | (kg/h) | (%) | (kg/h) | (%) | (kg/h) | (%) |
| | | | | | 0.0 | 0.00 | | |
| Propylene | 0.0 | 0.00 | 195.1 | 7.40 | 0.0 | 0.00 | 195.1 | 64.58 |
| Propane | 0.0 | 0.00 | 12.9 | 0.49 | 0.000 | 0.00 | 12.9 | 4.27 |
| Propylene Oxide (PO) | 0.000 | 0.00 | 5.47 | 0.21 | 0.00 | 0.00 | 48.7 | 16.13 |
| Methanol (MeOH) | 1966.69 | 81.20 | 1966.1 | 74.81 | 2066.09 | 81.92 | 45.0 | 14.90 |
| Water (H$_2$O) | 442.77 | 18.28 | 444.81 | 16.88 | 445.20 | 17.65 | 0.38 | 0.13 |
| Hydrogen Peroxide (H$_2$O$_2$) | 4.2 | 0.17 | 0.2 | 0.01 | 0.2 | 0.01 | 0.0 | 0.00 |
| Methoxypropanol | 8.9 | 0.29 | 8.6 | 0.33 | 8.6 | 0.34 | 0.0 | 0.00 |
| 1,2-propanediol | 1.5 | 0.06 | 1.8 | 0.07 | 1.8 | 0.09 | 0.0 | 0.00 |
| THROUGHPUT | 2422.1 | 100 | 2635.0 | 100 | 2521.9 | 100 | 302.1 | 100 |
| Temperature | 50.00 | | 37.80 | | 88.20 | | 40.00 | |
| Pressure | 13.00 | | 1.80 | | 2.01 | | 1.10 | |

| | 25 | | 26 | | 27 | | 28 | |
|---|---|---|---|---|---|---|---|---|
| COMPONENTS | (kg/h) | (%) | (kg/h) | (%) | | | (kg/h) | (%) |
| Propylene | 10.000 | 90.62 | | | 948.39 | 93.94 | 3.00 | 0.53 |
| Propane | 1.035 | 9.38 | | | 61.16 | 6.06 | 0.29 | 0.05 |
| Oxide (PO) | | | 43.2530 | 22.88 | | | 415.52 | 73.60 |
| Methanol (MeOH) | | | 145.0020 | 76.71 | | | 145.00 | 25.68 |
| Water (H$_2$O) | | | 0.7700 | 0.41 | | | 0.77 | 0.14 |
| Hydrogen Peroxide (H$_2$O$_2$) | | | | | | | 0.00 | 0.00 |
| Methoxypropanol | | | | | | | 0.00 | 0.00 |
| 1,2-propanediol | | | | | | | | |
| Oxygen | | | | | | | | |
| NH4OH | | | | | | | | |
| NaOH | | | | | | | | |
| Nitrogen | | | | | | | | |
| THROUGHPUT | 11.0 | 100 | 189.0 | 100 | 1009.6 | 100 | 564.6 | 100 |
| Temperature | −14.30 | | 63.40 | | −14.50 | | 75.30 | |
| Pressure | 3.80 | | 1.68 | | 3.80 | | 3.88 | |

| | 29 | | 30 | | T1-2-3 | T4 | | |
|---|---|---|---|---|---|---|---|---|
| COMPONENTS | (kg/h) | (%) | (kg/h) | (%) | (%) | (%) | (kg/h) | (%) |
| Propylene | 2.9910 | 2.72 | 0.0090 | | | | | |
| Propane | 0.2850 | 0.26 | 0.0010 | | | | | |
| Oxide (PO) | 106.7210 | 97.02 | 265.543 | 99.09 | | | | |
| Methanol (MeOH) | 0.0020 | 0.00 | 0.0120 | | | | | |
| Water (H$_2$O) | 0.0010 | 0.00 | 0.0020 | | 90.00 | 70.00 | | |
| Hydrogen Peroxide (H$_2$O$_2$) | | | | | | | | |
| Methoxypropanol | | | | | | | | |
| 1,2-propanediol | | | | | | | | |
| Oxygen | | | | | | | | |
| NH4OH | | | | | 10.00 | | | |
| NaOH | | | | | | 30.00 | | |
| Nitrogen | 0.0000 | 0.00 | | | | | 1.00 | 100.00 |

TABLE 1-B-continued

| THROUGHPUT | 110.0 | 100 | 265.6 | 100 | 100 | 100 | 1.0 | 100 |
|---|---|---|---|---|---|---|---|---|
| Temperature | 37.60 | | 39.10 | | 30.00 | 30.00 | 30.00 | |
| Pressure | 1.20 | | 1.22 | | 16.00 | 16.00 | 16.00 | |

The invention claimed is:

1. A process for the continuous preparation of an olefinic oxide by direct oxidation of an olefin with hydrogen peroxide, which comprises:
   (a) feeding into a reaction zone containing an epoxidation catalyst the olefin, the hydrogen peroxide, and a buffer and a reaction solvent;
   (b) feeding the product of the reaction zone into a distillation zone to obtain a head product comprising olefinic oxide and unreacted olefin, and a tail product comprising unreacted hydrogen peroxide, reaction by-products and water and reaction solvent;
   (c) feeding the tail product of the distillation zone and an aqueous basic solution into a decomposition zone containing a decomposition catalyst to decompose hydrogen peroxide in the tail product;
   (d) feeding the mixture leaving the decomposition zone comprising oxygen, water and solvent, optionally together with an inert gas, into a phase separation zone to obtain at the top a gaseous phase containing oxygen, traces of solvent and optionally an inert gas, and at the bottom a liquid phase comprising water and reaction by-products and solvent,;
   (e) feeding the gaseous phase leaving the phase separation zone into a condensation zone to recover the residual solvent, and discharging the uncondensable compounds;
   (f) feeding the liquid phase leaving the phase separation zone and the solvent leaving the condensation zone into a further distillation zone to obtain at the top a solvent which is recycled into the reaction zone in step (a), and a tail product comprising water, the reaction by-products and the traces of solvent, which tail product is discarded;
   (g) feeding the head product from the distillation zone in step b), together with the vent products from the reactor zone in step a) into a further distillation zone to obtain a head product comprising unreacted olefin, which is recycled into the reaction zone in step a), and a tail product comprising the olefinic oxide;
   (h) feeding the tail product from the distillation zone in step g) into a purification zone to recover the residual olefin, which is recycled into the reaction zone in step a), a liquid phase comprising solvent, which is recycled into the distillation zone in step b) and the olefinic oxide.

2. A process according to claim 1 comprising:
   (a) feeding into a first reactor R1, in which is contained a catalyst comprising a titanium-containing zeolite held in suspension in liquid reaction medium, a first portion of an olefin charge, hydrogen peroxide, a solvent and a buffer;
   (b) filtering the liquid product from the first reactor R1 and feeding the filtered product into a first column C1 to obtain a head product comprising olefinic oxide and unreacted olefin, and a tail product comprising solvent, water and unreacted hydrogen peroxide;
   (c) feeding the tail product from the first column C1, together with a second portion of the olefin charge, hydrogen peroxide and buffer, into a second reactor R2;
   (d) filtering the liquid product from the second reactor R2 and feeding the filtered product into a second stripping column C2 to obtain a head product comprising olefinic oxide and unreacted olefin and a tail product comprising solvent and residual hydrogen peroxide;
   (e) feeding the tail product from the second column C2, a third portion of the olefin charge and buffer into a third reaction unit R3;
   (f) filtering the liquid product from the third reactor R3 and feeding the filtered product into a third stripping column C3 to obtain a head product comprising olefinic oxide and unreacted olefin, and a tail product comprising solvent, water and traces of hydrogen peroxide;
   (g) feeding into a decomposition unit R-4A/B containing a supported catalyst for decomposing the residual hydrogen peroxide to oxygen and water, the tail product from the third column C3 and an aqueous basic solution;
   (h) feeding into a phase separator (flash) V-4, the mixture leaving the decomposition unit R-4A/B, comprising solvent, oxygen, and water, together with an inert gas, preferably nitrogen, to obtain a liquid phase comprising solvent, water and reaction by-products and a gaseous phase comprising solvent, oxygen and inert gas;
   (i) feeding the gaseous phase leaving V4 into a condensation system to recover the entrained solvent, while the uncondensable compounds are discharged;
   (l) feeding the solvent leaving the condensation system, together with the liquid phase leaving V4, into a distillation column C6 to obtain at the top the solvent, which is recycled into the reaction unit (R1), and a tail product comprising the reaction water and water introduced with the hydrogen peroxide, the reaction by-products and the traces of solvent, which is discarded;
   (m) feeding the head product from the stripping column C1–C3, together with the reactor vent products, into a distillation column C4 to obtain a head product comprising the unreacted olefin, which is recycled into one or more of the reaction units R1 to R3, and a tail product comprising the olefinic oxide and traces of solvent and of unreacted olefin;
   (n) feeding the tail product from the distillation column into a purification section, to recover, unreacted residual olefin, which is recycled into one or more of the reaction units R1 to R3, olefinic oxide of commercial purity, and from the column tail, a liquid phase comprising solvent and olefinic oxide, which is recycled into the distillation column C3.

3. A process according to claim 1 in which the olefin is chosen from those of general formula (I)

in which: R1, R2, R3 and R4, which may be identical or different, are selected from hydrogen, an alkyl radical containing from 1 to 20 carbon atoms, an aryl radical, an alkylaryl radical containing from 7 to 20 carbon atoms, a cycloalkyl radical containing from 6 to 10 carbon atoms and an alkylcycloalkyl radical containing from 7 to 20 carbon atoms.

4. A process according to claim 3, in which the radicals R1, R2, R3 and R4 constitute pairs of saturated or unsaturated rings and, optionally contain one or more of a halogen atom, nitro or nitrile group, sulphonic group and esters thereof, carbonyl, hydroxyl, carboxylic, thiol, amine and ether groups.

5. A process according to claim 3, in which the olefins of formula (I) is selected from ethylene, propylene, allyl chloride, allyl alcohol, butenes, pentenes, hexenes, 1-hepteneoctene, 1-tridecene, mesityl oxide, isoprene, cyclooctene, cyclohexene and bicyclic compounds.

6. A process according to claim 5, in which the olefin is propylene.

7. A process according to claim 6, in which the propylene has a purity of greater than 70%.

8. A process according to claim 7, in which the propylene is derived from a steam-cracking stream with a minimum purity of 96%.

9. A process according to claim 1 in which the olefin fed into the reaction unit comprises a fresh olefin, recycled olefin or a mixture thereof.

10. A process according to claim 9, in which before the fresh olefin is introduced into the reaction unit, it is purified in the distillation column C4.

11. A process according to claim 1 in which the hydrogen peroxide is used as an aqueous solution with a minimum titre of 1% by weight.

12. A process according to claim 11, in which the hydrogen peroxide is used as an aqueous solution with a titre of greater than or equal to 35% by weight.

13. A process according to claim 1, in which an olefin/$H_2O_2$ molar ratio of between 10:1 and 1:10 is used.

14. A process according to claim 13, in which the olefin/$H_2O_2$ molar ratio is between 6:1 and 1:1.

15. A process according to claim 2 in which the hydrogen peroxide is fed into the reactors R1 and R2 in a feed ratio of between 90:10 and 10:90.

16. A process according to claim 15, in which the ratio between the feeds is between 60:40 and 40:60.

17. A process according to claim 16, in which the feed ratio is 50:50.

18. A process according to claim 1 in which the solvent comprises one or more solvents that are liquid at the epoxidation temperatures, that are compatible with hydrogen peroxide and that are capable of dissolving the olefin and the olefinic oxide produced.

19. A process according to claim 18, in which the solvent is chosen from alcohols, aqueous-alcoholic mixtures, ketones, ethers, esters, aliphatic, cycloaliphatic and aromatic hydrocarbons, halogenated hydrocarbons, or mixtures thereof.

20. A process according to claim 19, in which the alcohols are chosen from methanol, ethanol, isopropyl alcohol, t-butyl alcohol and cyclohexanol.

21. A process according to claim 19, in which the ketones are acetone, methyl ethyl ketone and acetophenone.

22. A process according to claim 19, in which the ethers are tetrahydrofuran and butyl ether.

23. A process according to claim 19, in which the solvent is methanol or acetone.

24. A process according to claim 19, in which the solvent is a methanol/water mixture with a weight ratio between the two of between 10/90 and 99/1.

25. A process according to claim 1 in which the buffer is chosen from aqueous ammonia, ammonium acetate, ammonium formate or a system comprising a nitrogenous base and a salt thereof with an organic or mineral acid.

26. A process according to claim 1 in which the buffer is fed continuously with one of the reagent flows fed into the epoxidation reactor, in an amount such as to maintain the pH of the reaction mixture, measured under the operating conditions, at a value above 5.

27. A process according to claim 26, in which the pH of the reaction mixture is maintained at a value of between 5.5 and 8.

28. A process according to claim 1 in which the epoxidation catalyst is chosen from titanium silicalites of MEI structure, titanium silicalites of MEL structure or of intermediate MFI/MEL structure, or titanium-containing β-zeolites of BEA structure.

29. A process according to claim 28, in which the catalyst is chosen from titanium silicalites having the following general formula (II):

$$xTiO_2 \cdot (1-x)SiO_2$$

in which x is between 0.0001 and 0.04.

30. A process according to claim 29, in which, in the titanium silicalite, some of the titanium is replaced with metals chosen from boron, aluminium, iron and gallium.

31. A process according to claim 28 in which the catalyst is in the form of a powder, pellets, microspheres, an extrudate.

32. A process according to claim 28 in which the catalyst is used in combination with a binder (co-gel) or support chosen from silica, alumina, silica-alumina, zeolites and active charcoal.

33. A process according to claim 1 in which the amount of catalyst used in the epoxidation reaction is between 1% and 15% by weight relative to the reaction mixture.

34. A process according to claim 33, in which the amount of catalyst is between 4% and 10% by weight relative to the reaction mixture.

35. A process according to claim 1 in which the epoxidation reaction is carried out at a temperature of between 20° C. and 150° C.

36. A process according to claim 35, in which the temperature is between 40° C. and 100° C.

37. A process according to claim 36, in which the temperature is between 55° C. and 90° C.

38. A process according to claim 2, in which the reactors R1 and R2 operate at a temperature of 55–75° C. and a pressure of 13 bar, and the reactor R3 operates at a temperature of 70–90° C. and a pressure of 8 bar.

39. A process according to claim 1 in which the reaction for decomposition of the residual hydrogen peroxide is carried out at a pH >10, at a temperature of between 80° C. and 90° C., with a residence time of between 1 and 10 minutes.

40. A process according to claim 39, in which the pH of the reaction for decomposition of the residual hydrogen peroxide is controlled by feeding an aqueous basic solution comprising alkali metal or alkaline-earth metal hydroxides or carbonates.

41. A process according to claim 1 in which the catalyst used in the reaction for decomposition of the residual hydrogen peroxide comprises a group VIII metal or oxide thereof.

42. A process according to claim 2 in which the epoxidation reactors are chosen from stirred reactors, bubble reactors, gas-lift reactors and continuous stirred tank reactors and plug flow reactors.

43. A process according to claim 42, in which the reactors R1, R2 and R3 are of the isothermic continuous stirred tank reactor type.

44. A process according to claim 2 in which the decomposition zone comprises fixed-bed tubular reactors arranged in series.

45. A process according to claim 1 in which the distillation zone in step b) comprises stripping columns which operate under the same operating conditions and the discharge at the top streams in vapour phase comprises unreacted olefin, olefinic oxide, inert gases and solvent vapours.

46. A process according to claim 2 in which the temperature at the bottom of the distillation zone in step g) C4 does not exceed 80° C., with residence times in the region of one minute.

47. A process according to claim 2 in which the purification zone in step h), C5 comprises two columns in series with a large number of plates and separates out:

i), at the top, residual vapours that are still present;

ii) at the bottom, a liquid stream containing solvent and olefinic oxide; and     iii) laterally, a liquid stream comprising an olefinic oxide with a purity of at least 99.8%.

48. A process according to claim 2 in which the heat of condensation recovered at the top of the distillation zone in step f), C6 is used to serve at least some of the boiling needs in the process.

49. A process according to claim 2 in which the olefin is chosen from those of general formula (I)

in which: R1, R2, R3 and R4, which may be identical or different, are selected from hydrogen, an alkyl radical containing from 1 to 20 carbon atoms, an aryl radical, an alkylaryl radical containing from 7 to 20 carbon atoms, a cycloalkyl radical containing from 6 to 10 carbon atoms and an alkylcycloalkyl radical containing from 7 to 20 carbon atoms.

* * * * *